United States Patent [19]

Suhir

[11] Patent Number: 6,119,527
[45] Date of Patent: Sep. 19, 2000

[54] METHOD AND APPARATUS FOR PROOF TESTING OPTICAL FIBERS

[75] Inventor: Ephraim Suhir, Randolph, N.J.

[73] Assignee: Lucent Technologies Inc., Murray Hill, N.J.

[21] Appl. No.: 09/158,426

[22] Filed: Sep. 21, 1998

[51] Int. Cl.[7] .................................................. G01N 3/08
[52] U.S. Cl. .............................. 73/830; 73/834; 73/800; 73/810
[58] Field of Search .............................. 73/826, 827, 828, 73/830, 831, 834, 835, 800, 160, 866, 810

[56] References Cited

U.S. PATENT DOCUMENTS

| | | | |
|---|---|---|---|
| 4,812,641 | 3/1989 | Ortiz, Jr. ................................. | 250/205 |
| 4,883,054 | 11/1989 | Fuller et al. ............................. | 606/12 |
| 5,076,104 | 12/1991 | Glaesemann et al. ................... | 73/830 |
| 5,596,901 | 1/1997 | Gloor ...................................... | 73/159 |

OTHER PUBLICATIONS

E. Suhir, "Calculated Stresses in Dual Coated Optical Fibers", Proceedings of ths SPE 46TH Annual Technical Conference & Exhibits (Antec 1988), pp. 398–404.

E. Suhir, "Optical Fiber Interconnect Subjected to a Not–Very–Small Ends Off–Set: Effect of the Reactive Tension", Materials Research Society Symposium Proceedings, vol. 531 (1998), pp. 201–207.

E. Suhir, "Mechanical Behavior of Materials in Microelectronic and Fiber–Optic Structures: Application of Analytical Modeling—Review", Materials Research Society Symposium Proceedings, vol. 226 (1991), pp. 269–277.

E. Suhir, "Stresses in a Partially Coated Optical Glass Fiber Subjected to the Ends Off–Set", Journal of Lightwave Technology, vol. 15, No. 11 (Nov. 1997), pp. 2091–2094.

E. Suhir, "The Effect of the Nonlinear Stress–Strain Relationship on the Mechanical Behavior of Optical–Glass Fibers", International Journal of Solids and Structures, vol. 30, No. 7 (1993), pp. 947–961.

*Primary Examiner*—Max Noori
*Attorney, Agent, or Firm*—Brown Raysman Millstein Felder & Steiner LLP

[57] ABSTRACT

A method, technique, and apparatus proof test an optical fiber interconnect by applying an ends off-set stress on the optical fiber until the optical fiber fails or breaks, either immediately (short-term strength), or as a result of the delayed-fracture/"static-fatigue" phenomenon for the given off-set, and, hence, for the given stress (long-term strength), imposed for the measured period of time. If, for instance, the short-term strength is addressed, the off-set is measured at the time of the failure, and the corresponding critical strain of the optical fiber is then predicted. In predicting the critical strain, the method and apparatus iteratively determine the total strain, including non-linear components thereof, for an optical fiber interconnect experiencing the measured ends off-set. The analytical model/method includes the steps of iteratively processing characteristic parameters associated with the optical fiber, and determining the non-linear strain associated with the optical fiber. The apparatus includes a processor for implementing the disclosed method.

20 Claims, 3 Drawing Sheets

METHOD AND APPARATUS FOR PROOF TESTING OPTICAL FIBERS

BACKGROUND OF THE INVENTION

The present invention relates to a method and technique which imposes an off-set and thus stresses an optical fiber for performing an accelerated proof test of the optical fiber.

In the prior art, methods are known for testing optical fiber, such as three and four point bending, tensile loading, and two point bending. Such methods suffer from various problems; for example, in three point bending, it is possible for a flaw to be located in an area having a small bending moment, while an area having the largest bending moment may not contain a flaw. The results of such a test may therefore indicate a reliable fiber when, in fact, the fiber may be unreliable. Tensile loading may be undesirable in that one end of the fiber must be affixed to a surface, and weights are attached to the other end of the fiber. Two point bending may also be disadvantageous, since this method focuses on a small area of a fiber, and then only one side of the fiber is in tension.

Thus, a need exists for alternative methods for testing longer portions of optical fibers, which also do not suffer the problems of such testing methods in the prior art.

Optical fiber interconnects have been considered in the prior art which have been clamped at the ends and then subjected to not-very-small lateral ends off-set. The term "not-very-small" is defined herein to mean that the off-set is sufficiently small to apply elementary or linear beam theory to predict the stresses and strains for the given off-set, but also that the off-set is large enough so that the reactive tension is appreciable. Such reactive tension occurs because of an inability of the interconnect ends to move closer during its bending.

If the reactive tension is large, and so is the tensile stress, one has to consider the non-linear stress-strain relationship of the silica material in order to make a sufficiently accurate prediction of the induced stress. It has been found in the prior art that optical glass fibers subjected to tension exhibit a non-linear strain relationship. This can be described by the following expression:

$$\sigma = E_0 \varepsilon \left(1 + \frac{1}{2}\alpha\varepsilon\right), \quad (1)$$

in which $\sigma$ is the applied stress; $\varepsilon$ is the corresponding strain; $E_0$ is Young's modulus at low strain values of the optical fiber material (say, silica-based materials); and $\alpha$ is a parameter specifying the degree of non-linearity. Typically, $E_0 = 10.5 \times 10^6$ p.s.i. and $\alpha = 6$.

Accordingly, for a not-very-small lateral ends off-set of an optical fiber interconnect, the effect of the non-linear stress-strain relationship on the induced tensile strain/stress may be significant, and so such non-linear effects in the optical fiber interconnect should be accounted for in stress/strain measurements and designs.

SUMMARY OF THE INVENTION

A method, technique, and apparatus are disclosed which proof test an optical fiber interconnect by applying an ends off-set stress on the optical fiber. Depending on the objective of the testing, the off-set can be made so large, that the fiber breaks right away, or not that large, so that it will break later on because of the "static fatigue" (delayed fracture) phenomenon, or will not break at all within a certain (prescribed) period of time. If, for instance, the ultimate short-term strength is evaluated, the off-set is measured at the time of the failure, and the corresponding critical strain of the optical fiber is then predicted, based on the developed analytical stress model.

In predicting the critical strain, the disclosed method, technique, and apparatus iteratively determine the total strain, including non-linear components thereof, for an optical fiber interconnect experiencing the given (imposed) ends off-set. The theoretical model/method includes the steps of iteratively processing characteristic parameters associated with the optical fiber, and determining the non-linear strain associated with the optical fiber. The apparatus includes a processor for implementing the disclosed method.

DETAILED DESCRIPTION OF THE PREFERRED EMBODIMENT

Figure 1:
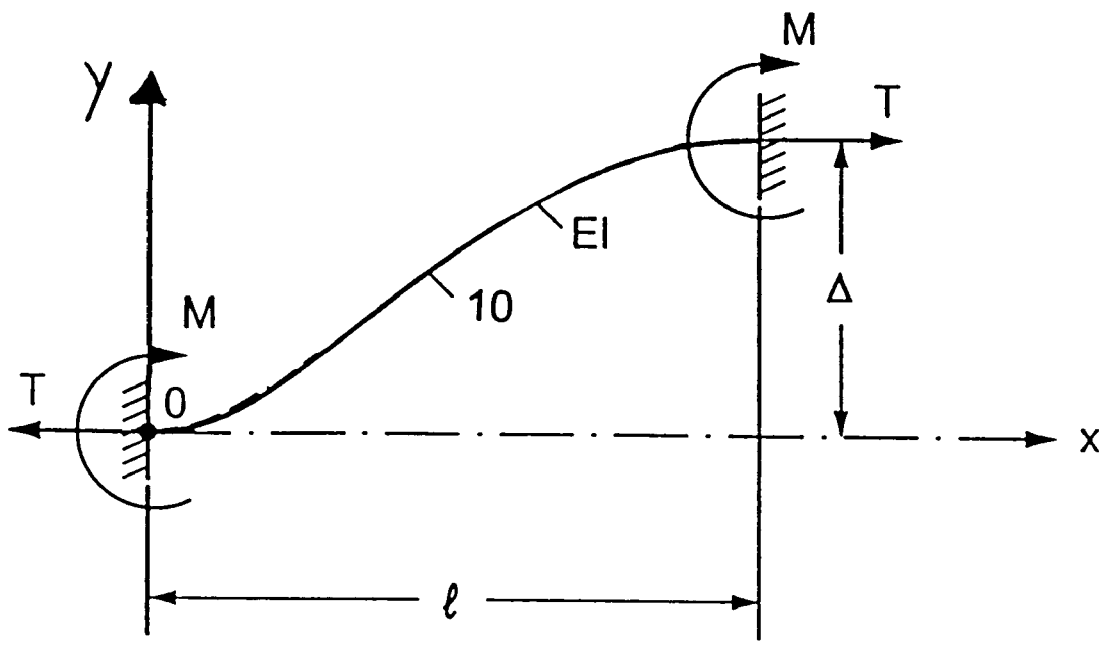
FIG. 1 illustrates the optical fiber interconnect and associated measurement values.

Referring now to FIG. 1, the optical fiber interconnect 10 under test is shown, which is subjected to an ends off-set and which is experiencing a combined action of bending and reactive tension until the optical fiber interconnect 10 breaks during the proof testing. The optical fiber interconnect 10 may be composed of, for example, silica-based material and the like. As shown in FIG. 1, the parameter $\Delta$ is the lateral ends off-set parameter measured along the y-axis, which, if the short-term strength of the fiber is considered, corresponds to the measured off-set at the time of the failure of the interconnect 10, and l is the interconnect span as the distance between supports, which is measured along the x-axis.

The forces T shown in FIG. 1 are the tensile forces, with associated bending moments M. A parameter EI associated with the optical fiber interconnect 10 is the flexural rigidity of the fiber. The interconnect 10 may be considered, from the standpoint of structural analysis, to be a prismatic single-span elastic beam clamped at the ends thereof. The length-to-diameter ratio of the interconnect 10 should be greater than 12, so that shearing effects are not of such significance to be accounted for. Also, in the overwhelming majority of cases, the shift in the neutral axis of the interconnect 10 (due to the non-linear stress-strain relationship) is small enough so that it does not significantly affect the elastic curve of the fiber, and need not be considered.

Figure 2:
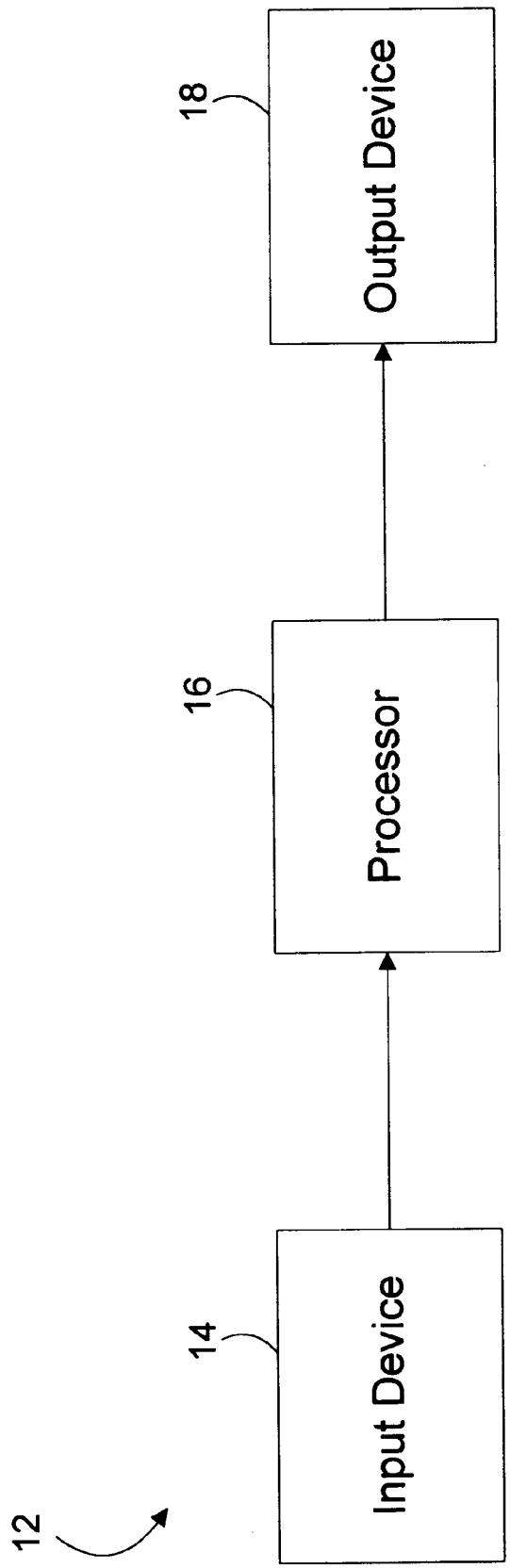
FIG. 2 illustrates a computer-based apparatus for determining the strain values from the measurement values.

The tensile strain $\varepsilon$ of the optical fiber interconnect 10 may be determined by, for example, a field tester who applies a tensile force to break the interconnect 10, and who measures the parameters associated with the interconnect 10 at the time of the break, as described above for FIG. 1. The field tester may then determine the strain from the input parameters using, for example, the apparatus 12 shown in FIG. 2 implementing the method shown in FIG. 3 and described herein. The apparatus 12 includes an input device 14, such as a computer keyboard or keypad for receiving the input parameters; a processor 16 such as a microprocessor-based device for executing software to implement the method of FIG. 3 to process the input parameters; and an output device 18 such as a liquid crystal display (LCD) for numerically displaying the tensile strain ϵ determined by the method of FIG. 3. In an illustrative embodiment, the apparatus 12 may be a portable "WINDOWS"—based device such as a laptop or a handheld computing device using "WINDOWS-CE", which executes the method shown in FIG. 3 implemented by compiled source code written, for example, in "VISUAL BASIC" or other programming languages. Alternatively, the apparatus 12 may be a programmable calculator such as the "HP-11" available from "HEWLETT-PACKARD".

Through the input device 14, values corresponding to the input parameters Δ and l, are input for processing by the processor 16. In addition, the fiber radius $r_0$ and the non-linearity parameter α may also be input, or may be predetermined or preset in the processor 16 for performing measurements in a series of comparable optical fiber interconnects. Such parameters Δ and l are characteristic parameters associated with the off-set of the interconnect 10, while the radius $r_0$ and the non-linearity parameter α are characteristic parameters associated with the composition of the interconnect 10.

The processor 16 may also include memory, which may be included in a microprocessor or which may be a memory chip separate from other processing components of the processor 16. Using the memory, the processor 16 may store and retrieve the input parameters such as the characteristic parameters, other initial or predetermined values, as well as any intermediate variables used in the method described herein to generate the tensile strain ϵ.

The tensile strain ϵ in an optical fiber interconnect 10 experiencing a not-very-small ends off-set can be expressed by $$\varepsilon = \left[\frac{u\Delta}{2l\Phi(u)}\right]^2 \quad (2)$$

with u and Φ being intermediate variables, in which $$u = kl = l\sqrt{\frac{T}{EI}} = 2\frac{l}{r_0^2}\sqrt{\frac{T}{\pi E}} = 2\frac{l}{r_0}\sqrt{2\varepsilon 2 + \frac{\alpha\varepsilon}{1+\alpha\varepsilon}} \quad (3)$$

is the parameter of the tensile force/stress.

In Equation (3), $$E = \frac{d\sigma}{d\varepsilon} = E_0(1+\alpha\varepsilon) \quad (4)$$

is Young's modulus of the silica material for a given finite strain ϵ, and $E_0$ is Young's modulus of the silica material for very low strains.

The function Φ is expressed as follows:

$$\Phi(u) = u\frac{1-\frac{2}{u}\tanh\frac{u}{2}}{\sqrt{3\left(1-\frac{2}{u}\tanh\frac{u}{2}\right)-\tanh^2\frac{u}{2}}}. \quad (5)$$

This function may be generated by the processor 16 using, for example, a mathematics co-processor, or which may be determined from Table 1 stored in the memory:

TABLE 1

| u | χ(u) | Φ(u) | $\overline{\Phi}_{(u)}$ | φ(u) | ψ(u) |
|---|---|---|---|---|---|
| 0 | 1.0000 | 0 | 0 | 1.0000 | 1.0000 |
| 0.5 | 0.9989 | 0.2915 | 0.3227 | 1.0004 | 1.0357 |
| 1.0 | 0.9952 | 0.6438 | 0.6455 | 1.0160 | 1.0637 |
| 1.5 | 0.9905 | 0.9685 | 0.9682 | 1.0364 | 1.0934 |
| 2.0 | 0.9842 | 1.2967 | 1.2910 | 1.0649 | 1.1207 |
| 3.0 | 0.9664 | 1.9544 | 1.9365 | 1.1411 | 1.1681 |
| 4.0 | 0.9451 | 2.6215 | 2.5820 | 1.2407 | 1.2049 |
| 5.0 | 0.9299 | 3.3541 | 3.3227 | 1.3888 | 1.2236 |
| 10.0 | 0.8333 | 6.7612 | 6.4550 | 2.0833 | 1.2958 |
| ∞ | 0.6667 | ∞ | ∞ | ∞ | 1.3535 |

The strain ϵ, solved from Equation (3), is:

$$\varepsilon = \frac{1}{\alpha}\left[\sqrt{1+\left(\frac{\alpha\eta}{2}\right)^2} + \frac{\alpha\eta}{2} - 1\right], \quad (6)$$

where:

$$\eta = \frac{1}{2}\left(\frac{ur_0}{2l}\right)^2 \quad (7)$$

The linear strain $\epsilon_0$ can be found to be:

$$\varepsilon_0 = \lim_{\alpha \to 0}\varepsilon = \frac{\eta}{2} \quad (8)$$

From Equations (6)–(8), the ratio $$\zeta = \frac{\varepsilon}{\varepsilon_0} \quad (9)$$

$$= \frac{2}{\alpha\eta}\left[\sqrt{1+\left(\frac{\alpha\eta}{2}\right)^2} + \frac{\alpha\eta}{2} - 1\right]$$

$$= 1 + \frac{\sqrt{1+(\overline{\alpha})^2} - 1}{\overline{\alpha}}$$

$$= 1 + \frac{\overline{\alpha}}{\sqrt{1+(\overline{\alpha})^2} + 1}$$

can be determined which considers the effect of the non-linear stress-strain relationship on the induced tensile strain, with $$\overline{\alpha} = \alpha\frac{\eta}{2} = \frac{\alpha}{4}\left(\frac{ur_0}{2l}\right)^2 \quad (10)$$

From Equations (2) and (6), the tensile force parameter u may be obtained from the following relationship:

$$\Phi(u) = \frac{1}{\sqrt{\zeta(u)}}\frac{\Delta}{r_0} \quad (11)$$

in which the u parameter may be solved iteratively from the input parameters, and the ζ ratio can also be determined iteratively therefrom.

The $i^{TH}$ iterative approximation of the strain value is:

$$\epsilon_i = \zeta_i \epsilon_0 \quad (12)$$

Accordingly, the strain value $\epsilon$ may be determined to be:

$$\varepsilon = \lim_{i \to \infty} \varepsilon_i \qquad (13)$$

and the iterations may be stopped after a sufficiently high accuracy is obtained.

Figure 3:
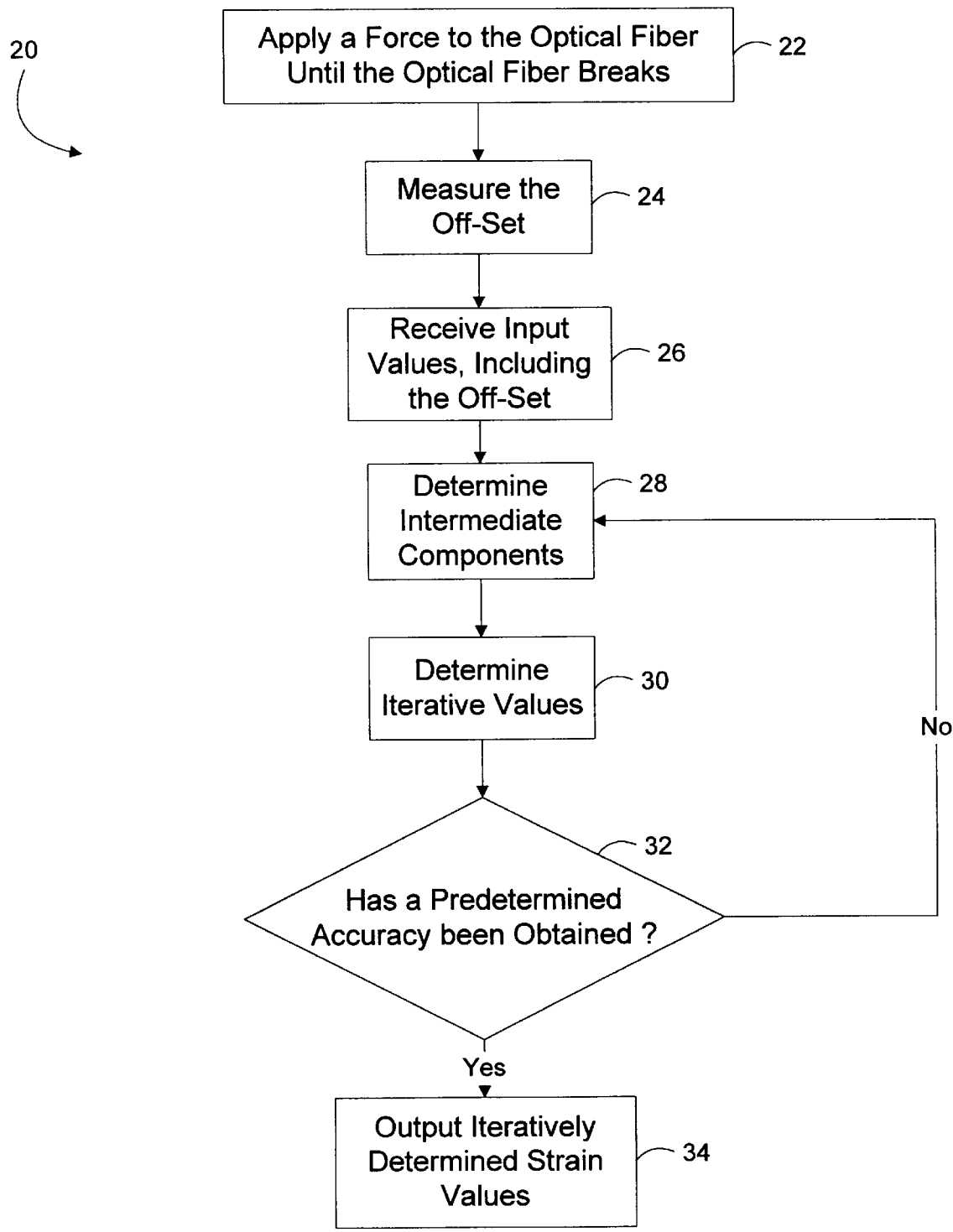
FIG. 3 illustrates an iterative method for determining the strain values.

In an illustrative embodiment, the method 20 of the present invention is shown in FIG. 3, having the steps of applying a tensile force F as shown in FIG. 1 to the optical fiber interconnect 10 in step 22 until the interconnect 10 breaks. The off-set $\Delta$ corresponding to the break in the interconnect 10 under test is then measured in step 24. The method further includes the steps of receiving the input parameters of the interconnect 10 under test in step 26, including receiving the off-set $\Delta$ corresponding to the break; determining intermediate components in step 28, such as the u parameter, from Equations (6)–(11); and determining iterative values in step 30, for example, iterations of the $\zeta$ ratio value and/or iterations $\epsilon_i$ of the strain $\epsilon$ using Equation (12).

The method then checks if a current iterative value has a predetermined and/or desired accuracy in step 32. For example, the method may compare successive iterations to determine if the difference therebetween is less than a predetermined error tolerance, such as 5%. Alternatively, the method may compare successive iterations to determine if both iterations have the same values to a predetermined number of significant digits, such as three digits to the right of the decimal.

If the predetermined accuracy has not been obtained, the method loops back to perform steps 28–32. If the predetermined accuracy is obtained, the current iterative values of $\zeta$ and/or $\epsilon$ having the requisite accuracy is used to determine the strain value $\epsilon$, which is then output as the iteratively determined strain value in step 34 using the output device 18. For example, the iteratively determined strain value may be displayed on an LCD device to be read by the field tester.

In an illustrative example, for an interconnect having a span l being about 3.0 mm, and a fiber radius $r_0$ of about 0.0625 mm, the interconnect 10 being proof-tested by experiencing a tensile force may break with an off-set $\Delta$ of about 0.6864 mm. Such values may be input and received in step 26, and a first iteration $\epsilon_1$ of the strain $\epsilon$ may be assumed to be the linear value $\epsilon_0$. Accordingly, a first approximation $\zeta_1$ of the $\zeta$ ratio is $\zeta_1(u)=\epsilon_1/\epsilon_0=1$, in which the non-linearity of the stress-stain curve is not considered.

From Equation (11), $\Phi_1(u)=10.9825$, from which $u_1$, as a first iterative approximation of the parameter u, may be determined to be $u_1=16$, for example, determined from Table 1. Accordingly, the linear strain $\epsilon_1=\epsilon_0=0.027777$. With $\alpha=6$ and $u=u_1=16$, Equation (10) is used to determine that $\bar{\alpha}_1=0.16667$.

After such initial calculations, the method then iteratively determines the non-linear strain $\epsilon$ using steps 28–32 in FIG. 3. In an second approximation, using Equation (9), step 28 is performed to calculate $\zeta_2=1.08276$, and so, using the above equations, such as Equation (11), the method determines in steps 28–32, that $\Phi_2(u)=10.5543, u_2=15.393, \bar{\alpha}_2=0.1542607, \zeta_3=1.076677;$
$\Phi_3(u)=10.5841, u_3=15.435, \bar{\alpha}_3=0.155037, \zeta_4=1.0770910;$ and
$\Phi_4(u)=10.5821, u_4=15.433, \bar{\alpha}_4=0.1550634, \zeta_5=1.077071.$ Accordingly, the last iterations for $\zeta_4$ and $\zeta_5$ are accurate to within four significant digits beyond the decimal point, and so in step 32, such a predetermined accuracy causes step 32 to be satisfied, so the iteration process ends. The method may then calculate the corresponding induced, non-linear strain to be $\epsilon=\epsilon_5=\zeta_5\epsilon_0=0.029918$, which is output in step 34, which is the strain which caused the interconnect 10 under test to fail in step 22.

As can be seen from the ratio $\zeta$, the total strain $\epsilon$, including non-linear components, may be significantly greater than the linear component $\epsilon_0$. From the above example, the last iteration $\zeta_5=1.077071$ demonstrates that the non-linear strain is at least 7.7% greater than the linear strain. Accordingly, by taking such non-linear components into account, the measurement of the strain on an optical fiber interconnect is greatly improved.

By the foregoing a novel and unobvious optical fiber testing method, technique, and apparatus have been disclosed by way of the preferred embodiment. However, numerous modifications and substitutions may be had without departing from the spirit of the invention. For example, while the preferred embodiment discusses a measurement method which may be implemented in a portable computing device, it is wholly within the preview of the invention to contemplate a network which receives remote measurements for generating such non-linear strain measurements at a distance from the location of the field test, in the manner as set forth above. Accordingly, the invention has been described by way of illustration rather than limitation.

What is claimed is:

1. A method for testing an optical fiber, comprising the steps of:

applying a force to the optical fiber until the optical fiber breaks;

iteratively processing a plurality of characteristic parameters associated with the optical fiber when the optical fiber breaks; and determining the non-linear strain at the time of the break and associated with the optical fiber from the iteratively processed characteristic parameters.

2. The method of claim 1 wherein the characteristic parameters include $\Delta$ as a lateral ends off-set parameter associated with the optical fiber.

3. The method of claim 1 wherein the characteristic parameters include l as an interconnect span being the distance between supports of the optical fiber.

4. The method of claim 1 wherein the characteristic parameters include a fiber radius $r_0$ of the optical fiber.

5. The method of claim 1 wherein the characteristic parameters include a non-linearity parameter $\alpha$ associated with the optical fiber.

6. The method of claim 1 wherein the step of iteratively processing includes the step of iteratively generating a ratio $\zeta$ from the characteristic parameters; and wherein the step of determining the non-linear strain includes the step of generating the non-linear strain from the ratio $\zeta=\epsilon/\epsilon_0$, in which $\epsilon$ is the non-linear strain of the optical fiber, and $\epsilon_0$ is a linear component of the non-linear strain.

7. The method of claim 6 wherein the step of iteratively generating the ratio $\zeta$ includes the step of:

iteratively generating the ratio $\zeta$ from the equations:

$$\zeta = \frac{\varepsilon}{\varepsilon_0} = \frac{2}{\alpha\eta}\left[\sqrt{1+\left(\frac{\alpha\eta}{2}\right)^2} + \frac{\alpha\eta}{2} - 1\right]$$

-continued $$= 1 + \frac{\sqrt{1+(\overline{\alpha})^2}-1}{\overline{\alpha}} = 1 + \frac{\overline{\alpha}}{\sqrt{1+(\overline{\alpha})^2}+1}$$

$$\overline{\alpha} = \alpha\frac{\eta}{2} = \frac{\alpha}{4}\left(\frac{ur_0}{2l}\right)^2$$

$$\Phi(u) = \frac{1}{\sqrt{\zeta(u)}}\frac{\Delta}{r_0} \quad \text{and}$$

$$\Phi(u) = u\frac{1 - \frac{2}{u}\tanh\frac{u}{2}}{\sqrt{3\left(1 - \frac{2}{u}\tanh\frac{u}{2}\right) - \tanh^2\frac{u}{2}}}$$

wherein $\Delta$ is a lateral ends off-set parameter associated with the optical fiber; l is an interconnect span being the distance between supports of the optical fiber; $r_0$ is a fiber radius of the optical fiber; $\alpha$ is a non-linearity parameter associated with the optical fiber; and u, $\eta$, $\Phi$, and $\overline{\alpha}$ are intermediate parameters derived from the aforesaid parameters associated with the optical fiber.

8. The method of claim 6 wherein the step of iteratively generating the ratio $\zeta$ includes the step of:
iteratively generating the ratio $\zeta$ until a desired accuracy in the value of the ratio $\zeta$ is attained between iterations.

9. A method for testing an optical fiber to measure the non-linear strain in an optical fiber interconnect experiencing an ends off-set using a computing device, comprising the steps of:
applying a force to the optical fiber until the optical fiber breaks;
receiving input values from an input device, with the input values being associated with a plurality of characteristic parameters at the time when the optical fiber breaks;
iteratively processing the characteristic parameters associated with the optical fiber interconnect using a processor of the computing device, the processor being connected to the input device;
determining the non-linear strain at the time of the break and associated with the optical fiber interconnect using the processor from the iteratively processed characteristic parameters; and
outputting a value associated with the determined non-linear strain using an output device connected to the processor.

10. The method of claim 9 wherein the characteristic parameters include $\Delta$ as a lateral ends off-set parameter associated with the optical fiber interconnect.

11. The method of claim 9 wherein the characteristic parameters include l as an interconnect span being the distance between supports of the optical fiber interconnect.

12. The method of claim 9 wherein the characteristic parameters include a fiber radius $r_0$ of the optical fiber interconnect.

13. The method of claim 9 wherein the characteristic parameters include a non-linearity parameter $\alpha$ associated with the optical fiber interconnect.

14. The method of claim 9 wherein the step of iteratively processing includes the step of iteratively generating a ratio $\zeta$ from the characteristic parameters using the processor; and
wherein the step of determining the non-linear strain includes the step of generating the non-linear strain from the ratio $\zeta=\epsilon/\epsilon_0$ using the processor, in which $\epsilon$ is the non-linear strain of the optical fiber, and $\epsilon_0$ is a linear component of the non-linear strain.

15. The method of claim 14 wherein the step of iteratively generating the ratio $\zeta$ includes the step of:
iteratively generating the ratio $\zeta$ using the processor from the equations:

$$\zeta = \frac{\varepsilon}{\varepsilon_0} = \frac{2}{\alpha\eta}\left[\sqrt{1+\left(\frac{\alpha\eta}{2}\right)^2}+\frac{\alpha\eta}{2}-1\right]$$

$$= 1 + \frac{\sqrt{1+(\overline{\alpha})^2}-1}{\overline{\alpha}} = 1 + \frac{\overline{\alpha}}{\sqrt{1+(\overline{\alpha})^2}+1}$$

$$\overline{\alpha} = \alpha\frac{\eta}{2} = \frac{\alpha}{4}\left(\frac{ur_0}{2l}\right)^2$$

$$\Phi(u) = \frac{1}{\sqrt{\zeta(u)}}\frac{\Delta}{r_0} \quad \text{and}$$

$$\Phi(u) = u\frac{1 - \frac{2}{u}\tanh\frac{u}{2}}{\sqrt{3\left(1 - \frac{2}{u}\tanh\frac{u}{2}\right) - \tanh^2\frac{u}{2}}}$$

wherein $\Delta$ is a lateral ends off-set parameter associated with the optical fiber; l is an interconnect span being the distance between supports of the optical fiber; $r_0$ is a fiber radius of the optical fiber; $\alpha$ is a non-linearity parameter associated with the optical fiber; and u, $\eta$, $\Phi$, and $\overline{\alpha}$ are intermediate parameters derived from the aforesaid parameters associated with the optical fiber.

16. The method of claim 14 wherein the step of iteratively generating the ratio $\zeta$ includes the step of:
iteratively generating the ratio $\zeta$ until a desired accuracy in the value of the ratio $\zeta$ is determined by the processor to have been attained between iterations.

17. An apparatus for proof testing an optical fiber interconnect experiencing a tensile force to break the optical fiber interconnect, and for measuring the non-linear strain at the time of the break in the optical fiber interconnect, comprising:
an input device for receiving input values associated with characteristic parameters corresponding to the optical fiber interconnect at the time of the break thereof;
a processor, connected to the input device, for receiving the input values therefrom, for iteratively processing the characteristic parameters associated with the optical fiber interconnect, and for determining the non-linear strain at the time of the break and associated with the optical fiber interconnect; and
an output device, connected to the processor, for outputting a value associated with the determined non-linear strain at the time of the break of the optical fiber interconnect.

18. The apparatus of claim 17 wherein the processor iteratively generates a ratio $\zeta$ from the characteristic parameters, and determines the non-linear strain from the ratio $\zeta=\epsilon/\epsilon_0$, in which $\epsilon$ is the non-linear strain of the optical fiber, and $\epsilon_0$ is a linear component of the non-linear strain.

19. The apparatus of claim 18 wherein the processor iteratively generates the ratio $\zeta$ by implementing the equations:

$$\zeta = \frac{\varepsilon}{\varepsilon_0} = \frac{2}{\alpha\eta}\left[\sqrt{1+\left(\frac{\alpha\eta}{2}\right)^2}+\frac{\alpha\eta}{2}-1\right]$$

-continued $$= 1 + \frac{\sqrt{1+(\overline{\alpha})^2}-1}{\overline{\alpha}} = 1 + \frac{\overline{\alpha}}{\sqrt{1+(\overline{\alpha})^2}+1}$$

$$\overline{\alpha} = \alpha \frac{\eta}{2} = \frac{\alpha}{4}\left(\frac{ur_0}{2l}\right)^2$$

$$\Phi(u) = \frac{1}{\sqrt{\zeta(u)}} \frac{\Delta}{r_0} \quad \text{and}$$

$$\Phi(u) = u \frac{1 - \frac{2}{u}\tanh\frac{u}{2}}{\sqrt{3\left(1 - \frac{2}{u}\tanh\frac{u}{2}\right) - \tanh^2\frac{u}{2}}}$$

wherein $\Delta$ is a lateral ends off-set parameter associated with the optical fiber; l is an interconnect span being the distance between supports of the optical fiber; $r_0$ is a fiber radius of the optical fiber; $\alpha$ is a non-linearity parameter associated with the optical fiber; and u, $\eta$, $\Phi$, and $\overline{\alpha}$ are intermediate parameters derived from the aforesaid parameters associated with the optical fiber.

20. The apparatus of claim 17, wherein the input device, output device, and processor are implemented in a portable computing device for proof testing the optical fiber interconnect.

* * * * *